(12) United States Patent
Horn

(10) Patent No.: US 9,885,671 B2
(45) Date of Patent: Feb. 6, 2018

(54) MINIATURIZED IMAGING APPARATUS FOR WAFER EDGE

(71) Applicant: KLA-Tencor Corporation, Milpitas, CA (US)

(72) Inventor: Paul D. Horn, Milpitas, CA (US)

(73) Assignee: KLA-Tencor Corporation, Milpitas, CA (US)

(*) Notice: Subject to any disclaimer, the term of this patent is extended or adjusted under 35 U.S.C. 154(b) by 0 days.

(21) Appl. No.: 14/731,861

(22) Filed: Jun. 5, 2015

(65) Prior Publication Data

US 2015/0355106 A1    Dec. 10, 2015

Related U.S. Application Data

(60) Provisional application No. 62/009,479, filed on Jun. 9, 2014.

(51) Int. Cl.
*G01N 21/00* (2006.01)
*G01N 21/95* (2006.01)
(Continued)

(52) U.S. Cl.
CPC ......... *G01N 21/9503* (2013.01); *G01N 21/47* (2013.01); *G01N 21/8806* (2013.01);
(Continued)

(58) Field of Classification Search
CPC .......... G01N 2021/8816; G01N 21/47; G01N 21/8806; G01N 21/9503; G01N 2201/062; G01N 2201/0634; G01N 2201/068
(Continued)

(56) References Cited

U.S. PATENT DOCUMENTS

| | | |
|---|---|---|
| 5,440,391 A | 8/1995 | Smeyers et al. |
| 5,511,934 A | 4/1996 | Bacchi et al. |

(Continued)

FOREIGN PATENT DOCUMENTS

| | | |
|---|---|---|
| AT | 531075 T | 11/2011 |
| CN | 101292263 A | 10/2008 |

(Continued)

OTHER PUBLICATIONS

Matthias, T., "Thin wafer processing—yield enhancement through integrated metrology", Electronics Packaging Technology Conference (EPTC), IEEE 13th, Dec. 2011, pp. 113-116.

(Continued)

*Primary Examiner* — Tri T Ton
(74) *Attorney, Agent, or Firm* — Kwan & Olynick, LLP

(57) ABSTRACT

Disclosed are methods and apparatus for imaging a rounded edge of a sample, such as a wafer with a beveled edge. In one embodiment, the system includes a curved diffuser having an internal surface for positioning towards the rounded edge of the sample and an external surface opposite the internal surface and light sources for generating a plurality of illumination beams adjacent to a plurality of positions on the external surface of the diffuser so that the diffuser outputs uniform light onto the rounded edge of the sample at a wide range of incident angles. The system further includes a sensor for receiving light scattered from the rounded edge of the sample in response to the incident light and generating a detected signal for generating an image. These elements are partially or entirely integrated into a compact assembly.

20 Claims, 9 Drawing Sheets

(51) Int. Cl.
  *G01N 21/88* (2006.01)
  *G01N 21/47* (2006.01)
(52) U.S. Cl.
  CPC ............ *G01N 2021/8816* (2013.01); *G01N 2201/062* (2013.01); *G01N 2201/068* (2013.01); *G01N 2201/0634* (2013.01)
(58) Field of Classification Search
  USPC ................ 356/237.1–237.6, 239.1–239.8
  See application file for complete search history.

(56) References Cited

U.S. PATENT DOCUMENTS

| | | | |
|---|---|---|---|
| 5,957,618 | A | 9/1999 | Sims et al. |
| 6,208,411 | B1 | 3/2001 | Vaez-Iravani |
| 6,248,988 | B1 | 6/2001 | Krantz |
| 6,324,298 | B1 | 11/2001 | O'dell et al. |
| 6,552,803 | B1 | 4/2003 | Wang et al. |
| 6,657,216 | B1 | 12/2003 | Poris |
| 6,707,608 | B1 | 3/2004 | Arieli et al. |
| 6,745,637 | B2 | 6/2004 | Tegeder et al. |
| 6,773,935 | B2 | 8/2004 | Watkins et al. |
| 6,778,282 | B1 | 8/2004 | Smets et al. |
| 6,954,267 | B2 | 10/2005 | Abraham et al. |
| 6,970,238 | B2 | 11/2005 | Gerhard et al. |
| 7,012,631 | B2 | 3/2006 | Vodanovic |
| 7,019,841 | B2 | 3/2006 | Mathur |
| 7,102,743 | B2 | 9/2006 | Tsuji et al. |
| 7,130,039 | B2 | 10/2006 | Vaez-iravani et al. |
| 7,142,300 | B2 | 11/2006 | Rosengaus |
| 7,149,341 | B2 | 12/2006 | Hayashi et al. |
| 7,158,235 | B2 | 1/2007 | Mathur |
| 7,197,178 | B2 | 3/2007 | Simpkins |
| 7,220,034 | B2 | 5/2007 | Li |
| 7,222,720 | B2 | 5/2007 | Truyens |
| 7,231,081 | B2 | 6/2007 | Snow et al. |
| 7,268,867 | B2 | 9/2007 | Vollrath et al. |
| 7,280,197 | B1 | 10/2007 | Rosengaus |
| 7,280,200 | B2 | 10/2007 | Plemmons |
| 7,326,929 | B2 | 2/2008 | Chou |
| 7,327,470 | B2 | 2/2008 | Arieli et al. |
| 7,359,068 | B2 | 4/2008 | Yonescu |
| 7,361,921 | B2 | 4/2008 | Gerhard |
| 7,382,450 | B2 | 6/2008 | Heiden |
| 7,397,553 | B1 | 7/2008 | Mehanian et al. |
| 7,433,034 | B1 | 10/2008 | Huang |
| 7,446,868 | B1 | 11/2008 | Higgs et al. |
| 7,477,370 | B2 | 1/2009 | Michelsson et al. |
| 7,477,401 | B2 | 1/2009 | Marx et al. |
| 7,489,394 | B2 | 2/2009 | Wienecke et al. |
| 7,508,504 | B2 | 3/2009 | Jin et al. |
| 7,511,293 | B2 | 3/2009 | Raymond et al. |
| 7,589,834 | B2 | 9/2009 | Higgs |
| 7,593,565 | B2 | 9/2009 | Reich et al. |
| 7,599,545 | B2 | 10/2009 | Shibata et al. |
| 7,616,804 | B2 | 11/2009 | Pai et al. |
| 7,656,519 | B2 | 2/2010 | Meeks et al. |
| 7,724,358 | B2 | 5/2010 | Vaughnn |
| 7,728,965 | B2 | 6/2010 | Haller et al. |
| 7,738,113 | B1 | 6/2010 | Marx et al. |
| 7,804,641 | B2 | 9/2010 | Hammond et al. |
| 7,813,541 | B2 | 10/2010 | Sali et al. |
| 7,835,566 | B2 | 11/2010 | Reich et al. |
| RE42,481 | E | 6/2011 | Wang et al. |
| 7,960,981 | B2 | 6/2011 | Strom et al. |
| 7,968,859 | B2 | 6/2011 | Young et al. |
| 8,045,788 | B2 | 10/2011 | Watkins et al. |
| 8,089,622 | B2 | 1/2012 | Birkner et al. |
| 8,175,372 | B2 | 5/2012 | Pai et al. |
| 8,194,301 | B2 | 6/2012 | Zhao et al. |
| 8,289,509 | B2 | 10/2012 | Wenz |
| 8,312,772 | B2 | 11/2012 | Tas et al. |
| 8,339,594 | B2 | 12/2012 | Sakamoto |
| 8,358,831 | B2 | 1/2013 | Doe |
| 8,380,472 | B2 | 2/2013 | Wang et al. |
| 8,395,783 | B2 | 3/2013 | Donaher et al. |
| 8,426,223 | B2 | 4/2013 | Voges et al. |
| 8,428,393 | B2 | 4/2013 | Kraft |
| 8,492,178 | B2 | 7/2013 | Carlson et al. |
| 9,645,097 | B2 | 5/2017 | Nicolaides et al. |
| 2003/0169916 | A1* | 9/2003 | Hayashi ............ G01N 21/9503 382/145 |
| 2003/0196343 | A1 | 10/2003 | Abraham et al. |
| 2004/0051810 | A1 | 3/2004 | Vodanovic |
| 2004/0085549 | A1 | 5/2004 | Smets et al. |
| 2004/0207836 | A1 | 10/2004 | Chhibber et al. |
| 2004/0233403 | A1 | 11/2004 | Gerhard et al. |
| 2005/0007603 | A1 | 1/2005 | Arieli et al. |
| 2005/0030528 | A1 | 2/2005 | Geffen et al. |
| 2006/0013471 | A1 | 1/2006 | Flieswasser et al. |
| 2006/0087660 | A1 | 4/2006 | Zabolitzky et al. |
| 2006/0213537 | A1 | 9/2006 | Atalla |
| 2006/0233433 | A1 | 10/2006 | Flieswasser et al. |
| 2006/0249965 | A1 | 11/2006 | Gerhard et al. |
| 2007/0057164 | A1 | 3/2007 | Vaughnn et al. |
| 2007/0077136 | A1 | 4/2007 | Schenck |
| 2007/0247618 | A1 | 10/2007 | Graf et al. |
| 2007/0273891 | A1 | 11/2007 | Gerhard et al. |
| 2008/0013089 | A1 | 1/2008 | Ishii et al. |
| 2008/0030731 | A1* | 2/2008 | Jin .................... G01N 21/4738 356/369 |
| 2008/0088851 | A1 | 4/2008 | Arieli et al. |
| 2008/0124489 | A1 | 5/2008 | Yamamoto et al. |
| 2008/0212084 | A1 | 9/2008 | Watkins et al. |
| 2008/0281548 | A1 | 11/2008 | Algranati et al. |
| 2009/0059215 | A1 | 3/2009 | Mehanian et al. |
| 2009/0079987 | A1 | 3/2009 | Ben-Ezra et al. |
| 2009/0086483 | A1 | 4/2009 | Hahn et al. |
| 2009/0116726 | A1 | 5/2009 | Postolov et al. |
| 2009/0122304 | A1 | 5/2009 | Jin et al. |
| 2009/0161094 | A1 | 6/2009 | Watkins |
| 2010/0093910 | A1 | 4/2010 | Halahmi et al. |
| 2010/0194406 | A1 | 8/2010 | Corulli et al. |
| 2010/0239157 | A1 | 9/2010 | O'dell et al. |
| 2010/0245566 | A1 | 9/2010 | Lev et al. |
| 2010/0277717 | A1 | 11/2010 | Stern et al. |
| 2010/0305897 | A1 | 12/2010 | Strom |
| 2010/0321056 | A1 | 12/2010 | Strom et al. |
| 2011/0032534 | A1 | 2/2011 | Malinovich et al. |
| 2011/0037492 | A1 | 2/2011 | Seubert et al. |
| 2011/0085725 | A1 | 4/2011 | Pai et al. |
| 2011/0089965 | A1 | 4/2011 | Endres et al. |
| 2011/0094945 | A1 | 4/2011 | Cohen et al. |
| 2011/0102574 | A1 | 5/2011 | Cohen |
| 2011/0102771 | A1 | 5/2011 | Shapirov |
| 2011/0115903 | A1 | 5/2011 | Shalem et al. |
| 2011/0128371 | A1 | 6/2011 | Gastaldo et al. |
| 2011/0141267 | A1 | 6/2011 | Lev et al. |
| 2011/0141594 | A1 | 6/2011 | Vaughnn et al. |
| 2011/0149275 | A1 | 6/2011 | Nakano et al. |
| 2011/0154764 | A1 | 6/2011 | Wang et al. |
| 2011/0164129 | A1 | 7/2011 | Postolov et al. |
| 2011/0164806 | A1 | 7/2011 | Peleg et al. |
| 2011/0190429 | A1 | 8/2011 | Muhammad et al. |
| 2011/0199480 | A1 | 8/2011 | Lev et al. |
| 2011/0199764 | A1 | 8/2011 | Shapirov |
| 2011/0263049 | A1 | 10/2011 | Voges et al. |
| 2011/0268348 | A1 | 11/2011 | Vaughnn |
| 2012/0026489 | A1 | 2/2012 | Zhao et al. |
| 2012/0086796 | A1 | 4/2012 | Lewis et al. |
| 2013/0100441 | A1 | 4/2013 | Tagawa et al. |
| 2014/0253910 | A1 | 9/2014 | Lewis |

FOREIGN PATENT DOCUMENTS

| | | | |
|---|---|---|---|
| CN | 101355694 A | | 1/2009 |
| CN | 201207094 Y | | 3/2009 |
| CN | 201207118 Y | | 3/2009 |
| CN | 201210191 Y | | 3/2009 |
| CN | 101430362 A | | 5/2009 |
| CN | 101714180 A | | 5/2010 |
| CN | 201765193 U | | 3/2011 |
| DE | 102005014595 A1 | | 10/2006 |
| DE | 102005014596 B3 | | 1/2007 |

(56) References Cited

FOREIGN PATENT DOCUMENTS

| | | |
|---|---|---|
| EP | 1972887 A1 | 9/2008 |
| EP | 1466137 B1 | 4/2010 |
| EP | 2367200 A2 | 9/2011 |
| EP | 1112550 B1 | 10/2011 |
| IL | 105765 A | 9/1998 |
| IL | 162650 A | 9/2014 |
| JP | 2007218889 A | 8/2007 |
| JP | 2010002216 A | 1/2010 |
| KR | 20080056150 A | 6/2008 |
| KR | 1020090008463 | 10/2010 |
| KR | 20110082476 A | 7/2011 |
| TW | I275335 B | 3/2007 |
| TW | 200802630 A | 1/2008 |
| TW | 200802666 A | 1/2008 |
| TW | 200802670 A | 1/2008 |
| TW | 200804799 A | 1/2008 |
| TW | 200811414 A | 3/2008 |
| TW | 200813411 A | 3/2008 |
| TW | 200820364 A | 5/2008 |
| TW | 200821571 A | 5/2008 |
| TW | 200825433 A | 6/2008 |
| TW | 20080065584 A | 7/2008 |
| TW | 200839916 A | 10/2008 |
| TW | 200842399 A | 11/2008 |
| TW | 200844428 A | 11/2008 |
| TW | 200845259 A | 11/2008 |
| TW | 200848338 A | 12/2008 |
| TW | 200900678 A | 1/2009 |
| TW | 200902964 A | 1/2009 |
| TW | 200909326 A | 3/2009 |
| TW | 200910515 A | 3/2009 |
| TW | 200912292 A | 3/2009 |
| TW | 200912804 A | 3/2009 |
| TW | 200913822 A | 3/2009 |
| TW | 200916763 A | 4/2009 |
| TW | 200919612 A | 5/2009 |
| TW | 200920095 A | 5/2009 |
| TW | 200921037 A | 5/2009 |
| TW | 200935045 A | 8/2009 |
| TW | 200938766 A | 9/2009 |
| TW | 201000888 A | 1/2010 |
| TW | 201009326 A | 3/2010 |
| TW | 201018331 A | 5/2010 |
| TW | 201029084 A | 8/2010 |
| TW | 201101400 A | 1/2011 |
| TW | 201108125 A | 3/2011 |
| TW | 201109677 A | 3/2011 |
| TW | 201115667 A | 5/2011 |
| WO | WO02071046 A1 | 9/2002 |
| WO | 2005079154 A2 | 9/2005 |
| WO | 2005104658 A2 | 11/2005 |
| WO | 2006006150 A2 | 1/2006 |
| WO | 2006013563 A2 | 2/2006 |
| WO | 2007023487 A2 | 3/2007 |
| WO | 2007023500 A2 | 3/2007 |
| WO | 2007023501 A2 | 3/2007 |
| WO | WO2007023500 A2 | 3/2007 |
| WO | 2008007363 A2 | 1/2008 |
| WO | 2008015677 A2 | 2/2008 |
| WO | 2008053490 A2 | 5/2008 |
| WO | 2008090559 A1 | 7/2008 |
| WO | 2008090563 A2 | 7/2008 |
| WO | 2008102338 A1 | 8/2008 |
| WO | 2008102339 A1 | 8/2008 |
| WO | 2008152648 A2 | 12/2008 |
| WO | 2009010983 A2 | 1/2009 |
| WO | 2009024970 A2 | 2/2009 |
| WO | 2009024978 A2 | 2/2009 |
| WO | 2009047641 A2 | 4/2009 |
| WO | 2010061388 A1 | 6/2010 |
| WO | 2011004365 A1 | 1/2011 |
| WO | 2011044473 A1 | 4/2011 |
| WO | 2011060401 A1 | 5/2011 |

OTHER PUBLICATIONS

"U.S. Appl. No. 14/741,866, Notice of Allowance dated Mar. 16, 2017", 7 pgs.
"International Application Serial No. PCT/US2015/034952, Search Report dated Sep. 23, 2015", 5 pgs.
"International Application Serial No. PCT/US2015/036820, Search Report dated Sep. 30, 2015", 3 pgs.
"EPO Search Report Appl. No. 15805729.9 PCT/US2015034952", dated Sep. 7, 2017. 10 pages.

* cited by examiner

MINIATURIZED IMAGING APPARATUS FOR WAFER EDGE

CROSS-REFERENCE TO RELATED APPLICATION

This application claims priority of U.S. Provisional Patent Application No. 62/009,479, entitled "Miniaturized Imaging Method for Wafer Edges", and filed 9 Jun. 2014 by Paul Horn, which application is herein incorporated by reference in its entirety for all purposes.

TECHNICAL FIELD OF THE INVENTION

The invention generally relates to a field of wafer inspection and imaging. More particularly the present invention relates to apparatus and techniques for inspecting and imaging a rounded wafer edge.

BACKGROUND

Generally, the industry of semiconductor manufacturing involves highly complex techniques for fabricating integrating circuits using semiconductor materials which are layered and patterned onto a substrate, such as silicon. Due to the large scale of circuit integration and the decreasing size of semiconductor devices, the fabricated devices have become increasingly sensitive to defects. That is, defects which cause faults in the device are becoming increasingly smaller. The device can generally be required to be fault free prior to shipment to the end users or customers.

Various inspection systems are used within the semiconductor industry to detect defects on a semiconductor reticle or wafer. One type of inspection tool is an optical inspection system. In optical inspection systems, one or more radiation beams are directed towards the semiconductor wafer and a reflected and/or scattered beam is then detected. The detected beam may then be used to generate a detected electrical signal or an image, and such signal or image is then analyzed to determine whether defects are present on the wafer.

In a specific inspection application, the side of a wafer is imaged to obtain an image of edge region of such wafer. There is a continuing need for improved inspection techniques and apparatus for imaging such edge regions.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a system for imaging a rounded edge of a sample, such as a wafer with a beveled edge, is disclosed. The system includes a curved diffuser having an internal surface for positioning towards the rounded edge of the sample and an external surface opposite the internal surface and a plurality of light sources for generating a plurality of illumination beams adjacent to a plurality of positions on the external surface of the diffuser so that the diffuser outputs uniform light over the rounded edge of the sample at a plurality of incident angles. The system further includes a sensor for receiving light scattered from the rounded edge of the sample in response to the incident light and generating a detected signal for generating an image. The light sources, diffuser, and sensor are integrated into a compact format. In a specific implementation, the sensor has a diameter that is equal to or less than 3 mm. In another implementation, the light sources are positioned a distance between about 3 mm and 1 inch from the external surface of the diffuser.

In another implementation, the diffuser is dome shaped. In one aspect, the diffuser is shaped and sized to output uniform light over all the surfaces of the beveled edge of a wafer. In further aspect, the uniform light also covers a border area of the top surface of the wafer. In another example, the sensor is positioned in the diffuser with respect to the light sources so as to receive light scattered from a particular set of one or more surfaces of the beveled edge. In another embodiment, the sensor is mounted or bonded within a hole of the diffuser. In a further aspect, the sensor is recessed in the hole and with respect to the internal surface of the diffuser.

In another aspect, the system comprises a positioning mechanism to adjustably move the diffuser, light sources, and sensor to different positions so as to image different sets of one or more surfaces of the rounded edge. In another aspect, the system includes a support structure to which the light sources are affixed. In a specific implementation, the light sources are LED's (light emitting diodes) that are affixed to the external surface of the diffuser. In another feature, the diffuser includes slots through which the sample may be inserted, and the system further comprises a positioning mechanism for rotating the diffuser, light sources, and sensor in a plane that is parallel with the slots so that the sample moves through the slots of the diffuser and the sensor receives light from different incident angles.

In another embodiment, the system includes a plurality of sensors inserted in the diffuser to receive light at different incident angles. In another aspect, the light sources are in the form of a plurality of optical fibers for directing light from one or more light generators. In another aspect, the light sources are composed of electronic components for generating the illumination beams directly onto the diffuser without transporting such illumination beams to the diffuser via any optical elements.

In another embodiment, the invention pertains to an inspection system for inspecting a sample. The inspection system includes one or more embodiments of the above-described edge detection system for imaging a rounded edge of a sample. The inspection system further includes inspection optics for directing one or more second illumination beams towards a top surface of the sample, an inspection detector for receiving a detected signal or image in response to an output beam being scattered or reflected from or transmitted through the sample in response to the output beam being reflected or scattered from the sample, and a processor and memory that are configured to analyze or review the detected signal or image from the inspection detector to thereby detect defects on the sample and configured to analyze the detected signal or image from the system for imaging the rounded edge of the sample to thereby detect defects on a rounded edge of a sample.

These and other aspects of the invention are described further below with reference to the figures.

DETAILED DESCRIPTION OF EXAMPLE EMBODIMENTS

Figure 1A:
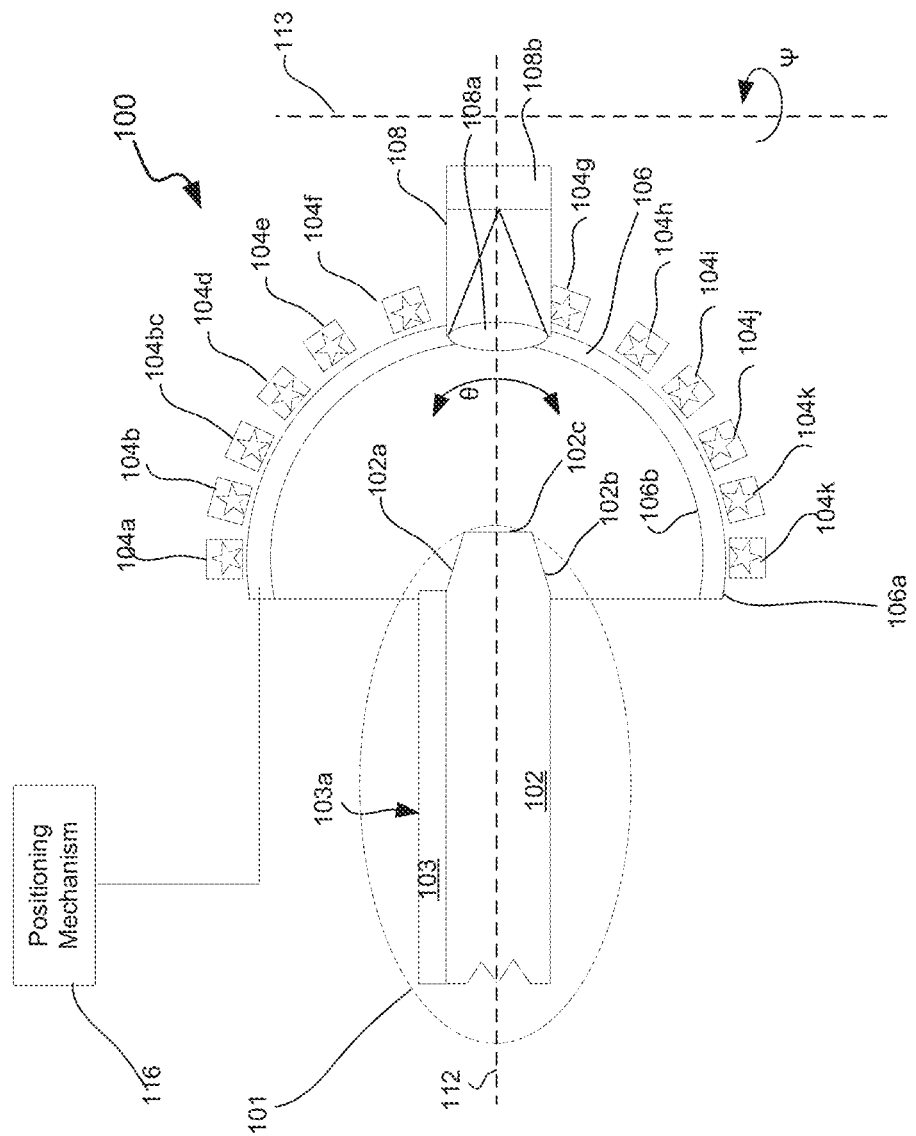
FIG. 1A is a diagrammatic cut-away side view of an edge detection system in accordance with one embodiment of the present invention.

In the following description, numerous specific details are set forth in order to provide a thorough understanding of the present invention. The present invention may be practiced without some or all of these specific details. In other instances, well known component or process operations have not been described in detail to not unnecessarily obscure the present invention. While the invention will be described in conjunction with the specific embodiments, it will be understood that it is not intended to limit the invention to the embodiments.

As used herein, the terms "specimen" and "sample" generally refer to a wafer or any other specimen having an edge on which defects of interest may be located. Although the terms "specimen", "sample", and "wafer" are used interchangeably herein, it is to be understood that embodiments described with respect to a wafer may be configured and/or used for inspection and imaging.

As used herein, the term "wafer" generally refers to substrates formed of a semiconductor or non-semiconductor material. Examples of a semiconductor material include, but are not limited to, monocrystalline silicon, gallium arsenide, and indium phosphide. Such substrates may be commonly found and/or processed in semiconductor fabrication facilities.

One or more layers may be formed upon a wafer. For example, such layers may include, but are not limited to, a resist, a dielectric material, and a conductive material. Many different types of layers are known in the art, and the term wafer as used herein is intended to encompass a wafer on which all types of layers may be formed or no layers yet formed. One or more layers formed on a wafer may be patterned. For example, a wafer may include a plurality of dies, each having repeatable pattern features. Formation and processing of such layers of material may ultimately result in completed semiconductor devices. In sum, a wafer may include a bare substrate on which no layers are formed, a substrate on which a portion of the layers of a complete semiconductor device have been formed, or a substrate on which all layers of a complete semiconductor device have been formed.

Wafers may contain defects in the edges of the wafers. Examples of defects that may be found in the edge of wafers include, but are not limited to, chips, cracks, scratches, marks, particles, and residual chemicals (e.g., resist and slurry). For example, while spin-coating the wafer with photoresist material, a photoresist bead may form around the wafer perimeter and excess photoresist may migrate down over the edge of the wafer. Such excess edge photoresist may flake off and migrate to the device areas of the wafer. Similarly, etch chemicals or deposition film materials may remain on the wafer edge and migrate to the device areas. Any number of these edge defects may result in yield loss. When multiple wafers are bonded together, the bond between such wafers may also have a defect.

Apparatus and techniques for inspecting a rounded or beveled sample edge, such as a wafer edge, for defects are described herein. In general, an edge detection system for uniformly illuminating and imaging very curved or rounded surfaces, such as beveled wafer edges, is provided. The edge detection generally includes a compact curved diffuser that can fit around a rounded edge, such as a beveled wafer edge, to which multiple light sources are provided to generate illumination at multiple positions on the diffuser surface.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

FIG. 1A is a diagrammatic cut-away side view of an edge detection system 100 in accordance with one embodiment of the present invention. The edge detection system 100 can detect defects on a beveled edge of sample. In this example, a cross-sectional wafer edge portion 101, which is the thinnest edge surface of a semiconductor wafer, is illustrated as the sample of interest. The wafer's edge may be beveled or rounded along the entire length. For instance, the sample 101 may merely comprise beveled edge portion 102. Alternatively as illustrated, the sample 101 may include both beveled edge portion 102 and non-beveled edge portion 103, for example, in a bonded wafer type arrangement in which multiple wafers are stacked and bonded together. In both examples, the wafer edge may be subject to a grinding, cutting or polishing process that results in a beveled edge. During such grinding, cutting or polishing, a portion of the edge may remain unbeveled. The beveled edge has top surface 102a, bottom surface 102b, and side surface 102c. The top and bottom surfaces 102a and 102b slope into the side surface 102c. However, the rounded edge may be formed by any suitable number of beveled facets.

The sample's top surface 103a may include one or more patterned layers or may be bare. The wafer may further include at least a portion of an integrated circuit, a thin-film head die, a micro-electro-mechanical system (MEMS) device, flat panel displays, magnetic heads, magnetic and optical storage media, other components that may include photonics and optoelectronic devices such as lasers, waveguides and other passive components processed on wafers, print heads, and bio-chip devices processed on wafers.

In general, the edge detection system has a very compact design that provides illumination for a wide range of incident angles so as to image all or a substantial portion of the beveled edge surfaces.

In the illustrated example, the edge detection system 100 is formed from a plurality of light sources (e.g., 104a~104k) and a compact sensing element 108 that are coupled with or adjacent to a miniaturized dome-shaped diffuser 106. Any suitable light sources that are very compact may be used. Example compact, small light sources include LED's (light emitting diodes), one or more light sources coupled with fiber optics, such as halogen lamps, diode lasers, etc. Any suitable image sensor that is very compact may be used. For instance, the sensor may have a diameter that is less than or equal to a few mm. Example sensors include the OmniVision OV6922, etc.

In certain embodiments, the entire edge detection system is very small, e.g., having a radius that is less than 25 mm, allowing the edge detection system 100 to be positioned relatively close to the edge of interest.

The diffuser 106 may be formed from a material that transmits and scatters (e.g., diffuses) light from the light sources so that light is scattered from the entire inner portion of the diffuser towards the beveled edge surfaces in a wide range of angles. The diffuser 106 may be machined from an optically diffuse material, such as fluoropolymer or Spectralon available from Labsphere, Inc. of North Sutton, N.H., polycarbonite resins, etc. Alternatively, the diffuser 106 can be generated with a 3D printer. The diffuser may also be formed from a diffuser film adhered to a transparent substrate that is positioned between the light sources and film. The internal surface of the diffuser 106b may also be coated with a reflective material so as to reflect the diffused light towards the inside of the dome and towards the beveled edge surfaces.

The diffuser may have any suitable shape so as to provide a surface through which illumination beams from the light sources may be transmitted and scattered so that light is emitted towards all surfaces or a substantial portion of all surfaces of the beveled edge. In the illustrated example, the diffuser 106 is dome-shaped into a size to cover the range of angles of incidence of the light sources.

In a specific implementation, the edge detection system 100 is positioned so as to provide illumination to all of the beveled edge surfaces and up to 10 or more mm into the border region on the top surface. It is also noted that the light is output from the entire surface of the dome to completely impinge on all sides of the beveled edge.

Figure 1B:
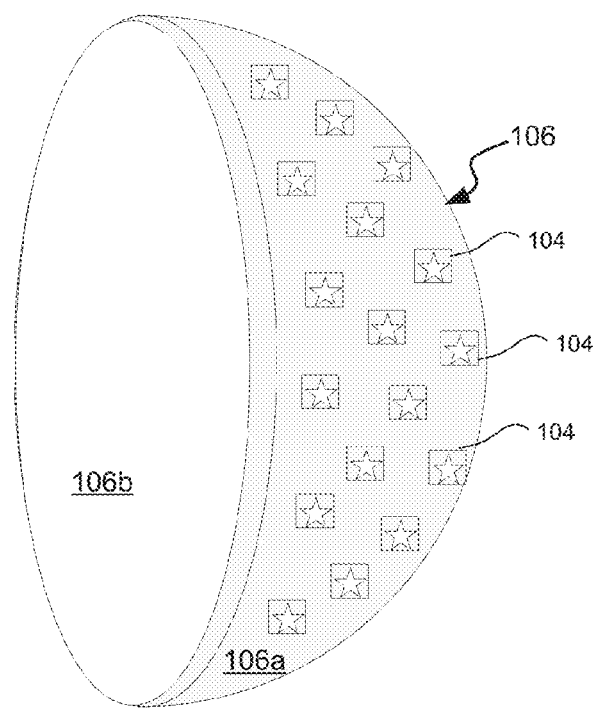
FIG. 1B is a perspective view of the diffuser of FIG. 1A in accordance with a specific implementation of the present invention.
Figure 1C:
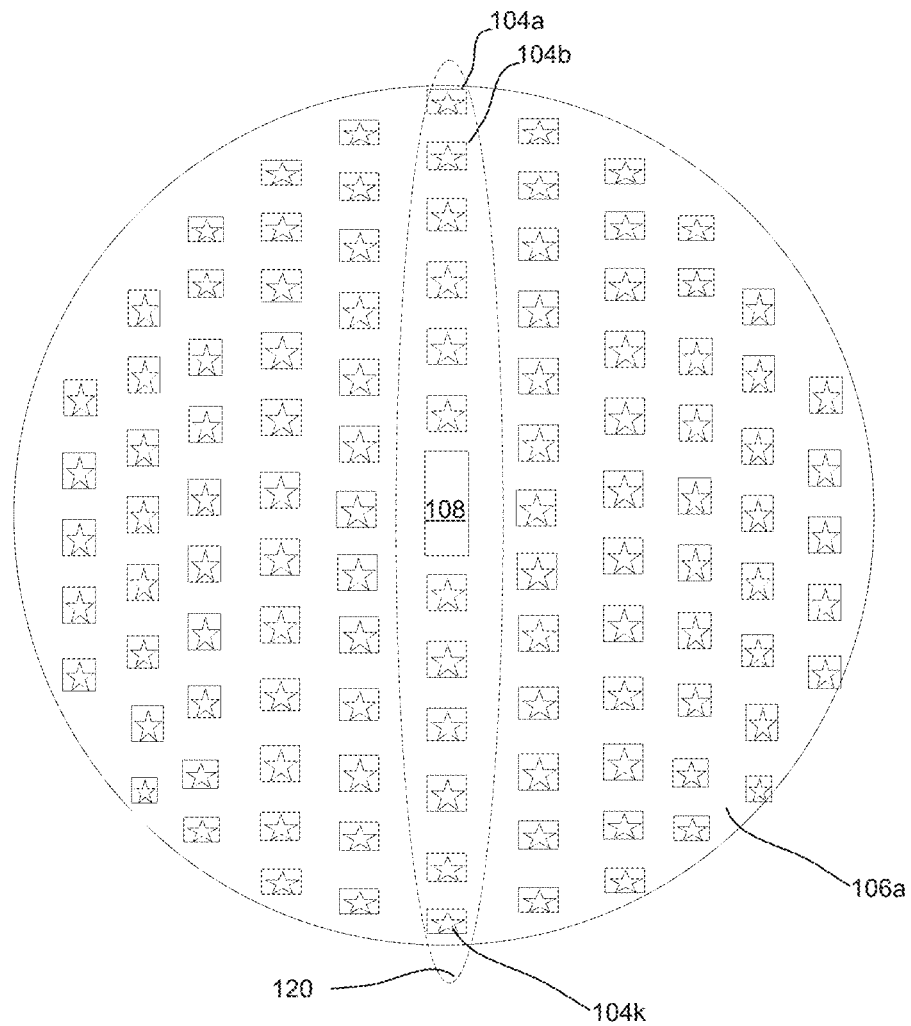
FIG. 1C is a diagrammatic back view illustrating the distribution of light sources over the external diffuser surface in accordance with one embodiment.

In either position, the light sources may be distributed across the range of incident angles. FIG. 1B is a perspective view of the diffuser of FIG. 1A in accordance with a specific implementation of the present invention. As shown, the light sources 104 are distributed over the entire external diffuser surface 106a although only a portion of the light sources are shown. FIG. 1C is a diagrammatic back view (looking towards the edge) illustrating the distribution of light sources over the external diffuser surface in accordance with one embodiment. As shown, the light sources 104 can be distributed around the sensor 108 and over the entire external surface 106a of the diffuser. The scale of the illustrated distributed light sources may differ from the actual design.

The light sources do not necessarily have to be distributed across the entire surface of the diffuser. By way of example, the light sources may be arranged along a single horizontal line (not shown) and/or a single vertical line (e.g., 120). Other arrangements, such as one or more ring patterns, one or more rectangle patterns, a random pattern, etc., are contemplated.

As a result of the diffuser and light source arrangement of the edge detection system, the light reflects and scatters from all of the surfaces on the bevel so as to be received by the sensor or camera. That is, a substantial portion or all of the beveled surfaces are imaged.

The camera or sensor 108 may also be positioned so as to receive scattered light from a particular set of one or more surfaces of the beveled edge (e.g., 102a~c). The sensor or camera 108 generally includes collection optics 108a for directing and focusing a portion of the light that was scattered from the edges-of-interest onto a detector/sensor 108b. The camera 108 may be integrated into the diffuser 106. For instance, the sensor 108 can be mounted or bonded within a hole or slot of the diffuser 106. The camera can mounted or bonded to be flush against the diffuser's internal surface 106b or be recessed below the diffuser surface.

As shown in FIG. 1A, for example, the camera 108 is positioned normal 112 to the side edge 102c so as to receive light from all of the beveled surfaces. The camera 108 may be adjustably or fixably positioned at any suitable angle to receive light from a particular set of one or more beveled surfaces. For instance, the diffuser, light sources, and sensor 108 can be rotated via positioning mechanism 116 to a plurality of positions (e.g., direction θ with respect to normal axis 112 or direction Ψ with respect to axis 113 of FIG. 1A) to view and image a particular set of one or more edge surfaces. The positioning mechanism 116 may take any form, such as a screw drive and stepper motor, linear drive with feedback position, or band actuator and stepper motor.

Figure 2:
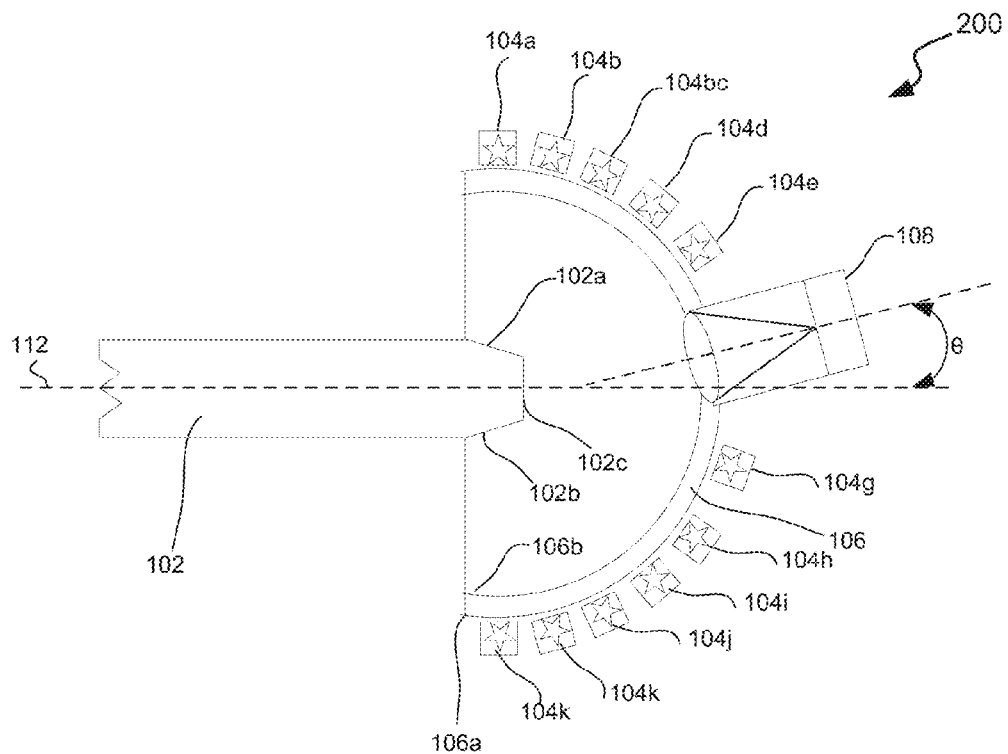
FIG. 2 illustrates a cut-away side view of an alternative edge detection system in which the sensor is mounted in the diffuser at an alternative position in accordance with a specific implementation of the present invention.

Alternatively, the sensor 108 can be fixably positioned at a different angle with respect to the diffuser 106. FIG. 2 illustrates a cut-away side view of an alternative edge detection system 200 in which the sensor is mounted in the diffuser at an alternative position. As shown, the light sources (e.g., 104a~e and 104g~k) are distributed asymmetrically with respect to sensor 108. For instance, there are 5 light sources distributed above and 6 light sources distributed below in a line with the sensor 108. The sensor 108 is also positioned at an angle θ from the normal 112.

Figure 3:
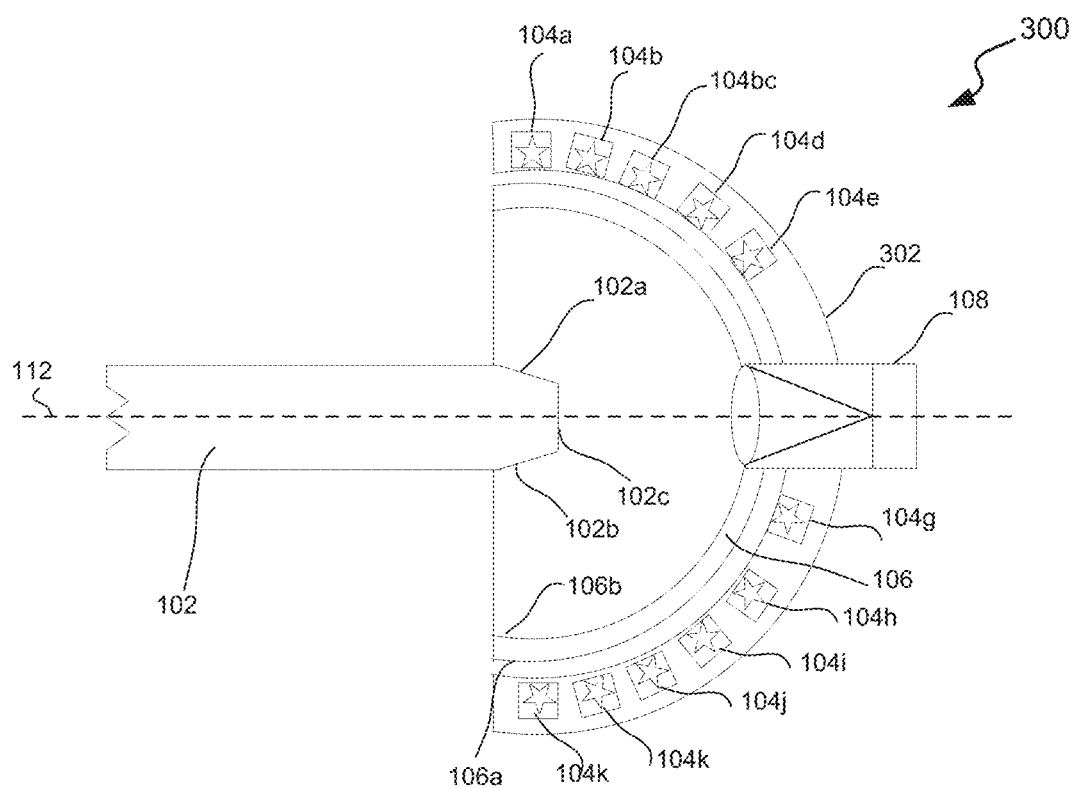
FIG. 3 is a cut-away side view of an edge detection system in which the light sources are mounted to a support piece that is separate and adjacent to the diffuser in accordance with an alternative embodiment.

The light sources (e.g., 104a~k) may be attached or positioned adjacent to the diffuser 106 in any suitable manner so as to form a compact edge detection system. Preferably, the distance between the light sources and the diffuser's external surface (e.g., 106a of FIG. 1A) has a range between 3 mm to about 1 inch. For example, LED's may be bonded to the external diffuser surface (e.g., 106a) that is opposite the internal diffuser surface (e.g., 106b), which faces the edge of interest. In another example, the light sources can be coupled to, affixed to, or integrated in another piece that is positioned adjacent to the diffuser's external surface. FIG. 3 is a cut-away side view of an edge detection system 300 in which the light sources are mounted to a support piece 302 that is separate and adjacent to the diffuser 106 in accordance with an alternative embodiment. The support piece 302 may comprise a single piece for holding all of the light sources or multiple pieces for holding different light sources. As shown, the support piece 302 is dome shaped to wrap around the diffuser when the support piece 302 is positioned adjacent to the diffuser 106.

Figure 4A:
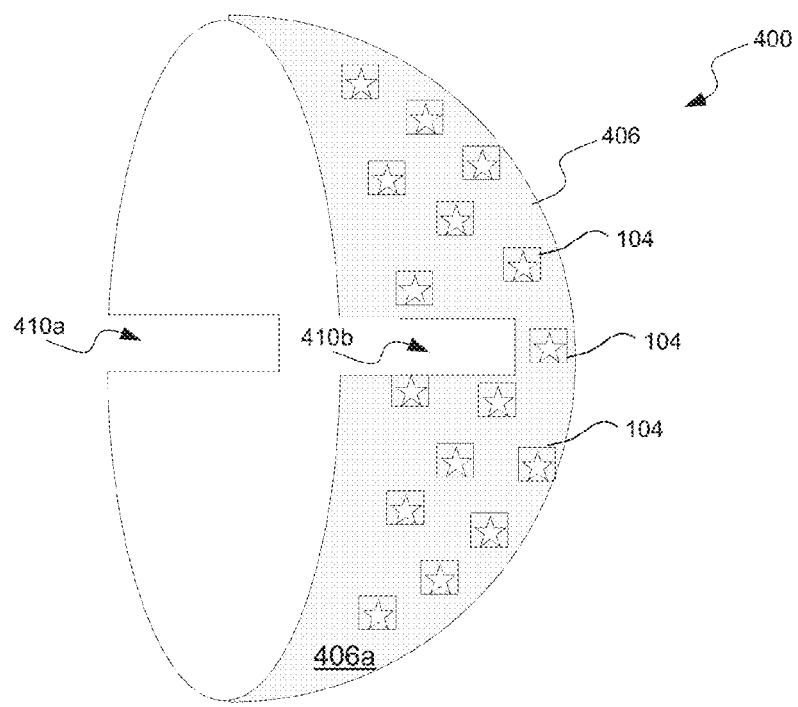
FIG. 4A is a perspective view of an edge detection system in accordance with an alternative embodiment of the present invention.
Figure 4B:
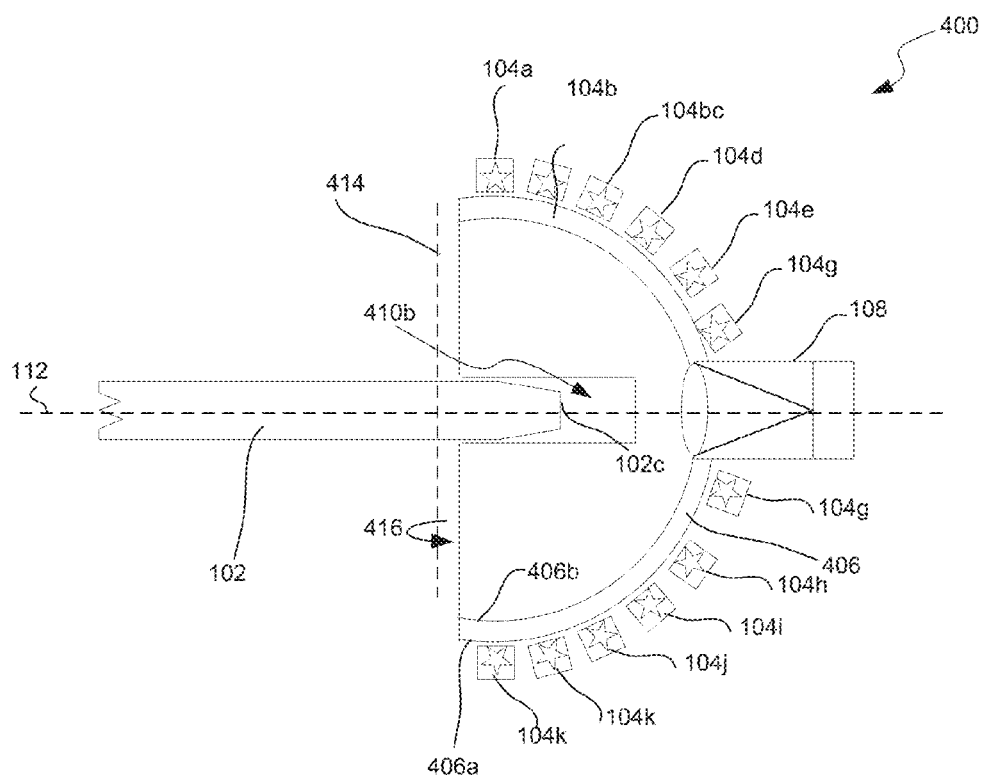
FIG. 4B is a cut-away side view of the edge detection system of FIG. 4A.

In other embodiments, the diffuser may be shaped to allow freedom of movement of the diffuser with respect to the sample while the sample is positioned close to the diffuser's internal surface and sensor. FIG. 4A is a perspective view of an edge detection system 400 in accordance with an alternative embodiment of the present invention. FIG. 4B is a cut-away side view of the edge detection system 400 of FIG. 4A. The diffuser 406 includes slots 410a and 410b into which the sample 102 may be inserted. The detection system 400 can then be rotated in a same plane as the sample 102, for example, around axis 414 in direction 416. Different azimuth angles (non-normal with respect to side edge 102c) may allow different structures or defects to be imaged with additional or different information, as compared to an image that is obtained with the sensor positioned along a normal axis with respect to the side edge 102c of the sample 102. That is, certain structures (e.g., repeating patterns) may be imaged more clearly if such structures are viewed from an oblique angle.

Figure 5:
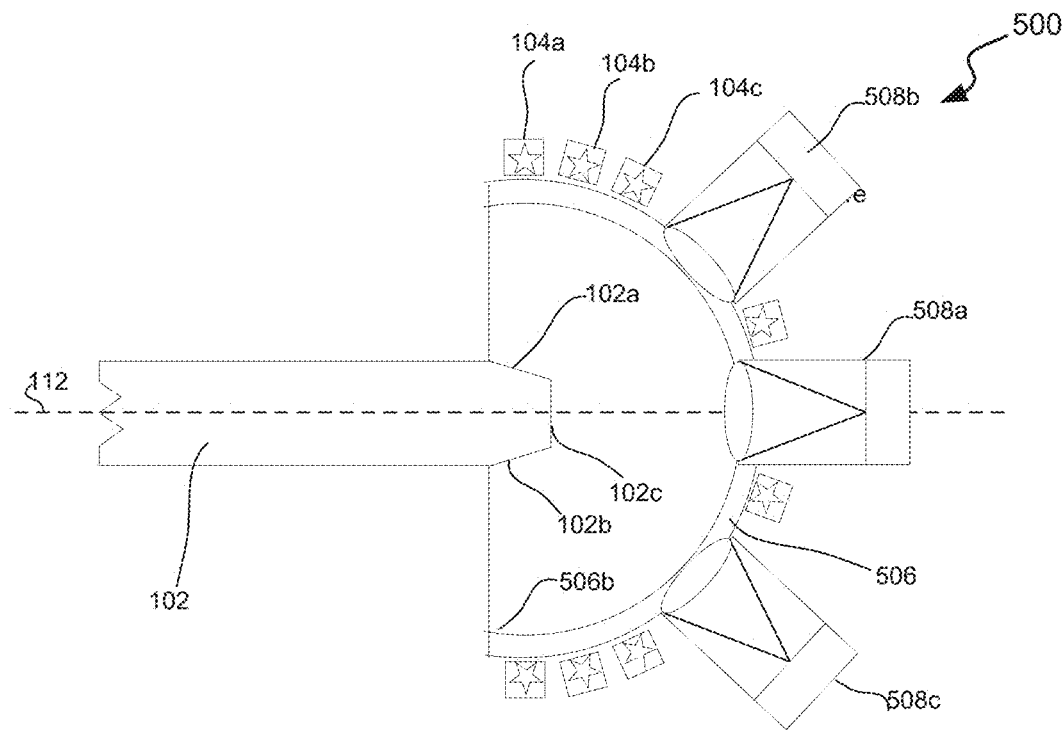
FIG. 5 is a cut-away side view of an edge detection system having multiple cameras in accordance with another embodiment of the present invention.

FIG. 5 is a cut-away side view of an edge detection system 500 having multiple cameras in accordance with another embodiment of the present invention. As shown, multiple cameras (e.g., 508a, 508b, and 508c) may be positioned within the diffuser 506. The different cameras may be utilized for any number of applications. For instance, each camera may be placed at a different angle with respect to the surface of interest. Each camera may also be configured to detect a particular range of wavelengths or colors. Of course, cameras that each are configured to detect multiple colors may alternatively be used in this embodiment or any embodiment described herein.

Figure 6:
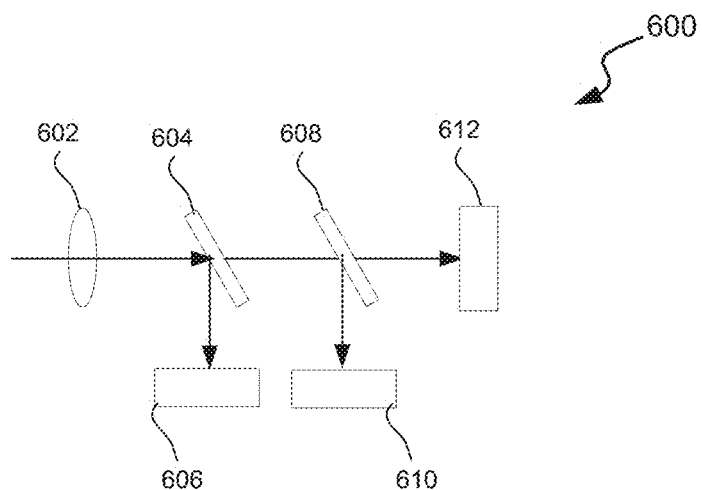
FIG. 6 is a diagrammatic representation of a sensor system in accordance with an alternative embodiment of the present invention.

FIG. 6 is a diagrammatic representation of a sensor system 600 in accordance with an alternative embodiment of the present invention. This sensor system is arranged to received and detect different colors or wavelength ranges. For example, detected light may be received by lens element 602, which directs the received light towards a first filter 604. The first filter 604 transmits a first set of wavelengths (e.g., red green) towards a second filter 608 and reflects a second set of wavelengths (e.g., blue) towards a first detector 606. The second filter 608 transmits a third set of wavelengths (e.g., red) towards a second detector 612 and reflects a fourth set of wavelengths (e.g., green) towards a third detector 610. Of course, the sensor may be configured to detect any suitable number of wavelength ranges by one or more detectors.

In certain embodiments, the edge detection system's components for generating, diffusing, and scattering light towards the sample are all electronic and do not include any optics for directing light from a remote location to the sample. That is, these edge detection systems do not require light to be remotely generated and directed towards the sample through bulky optical elements. Additionally, the embodiments in which the light sources are placed adjacent to the diffuser, a fewer number of light sources may be required to result in sufficient light for illuminating and imaging the rounded or beveled edge. Fewer light sources may also result in reduced heat load, lower power requirements, longer light source life, and less wear on the system. Certain embodiments of the edge detection system also provide a single, integrated unit that can easily be fitted into any suitable metrology or inspection tool.

Figure 7:
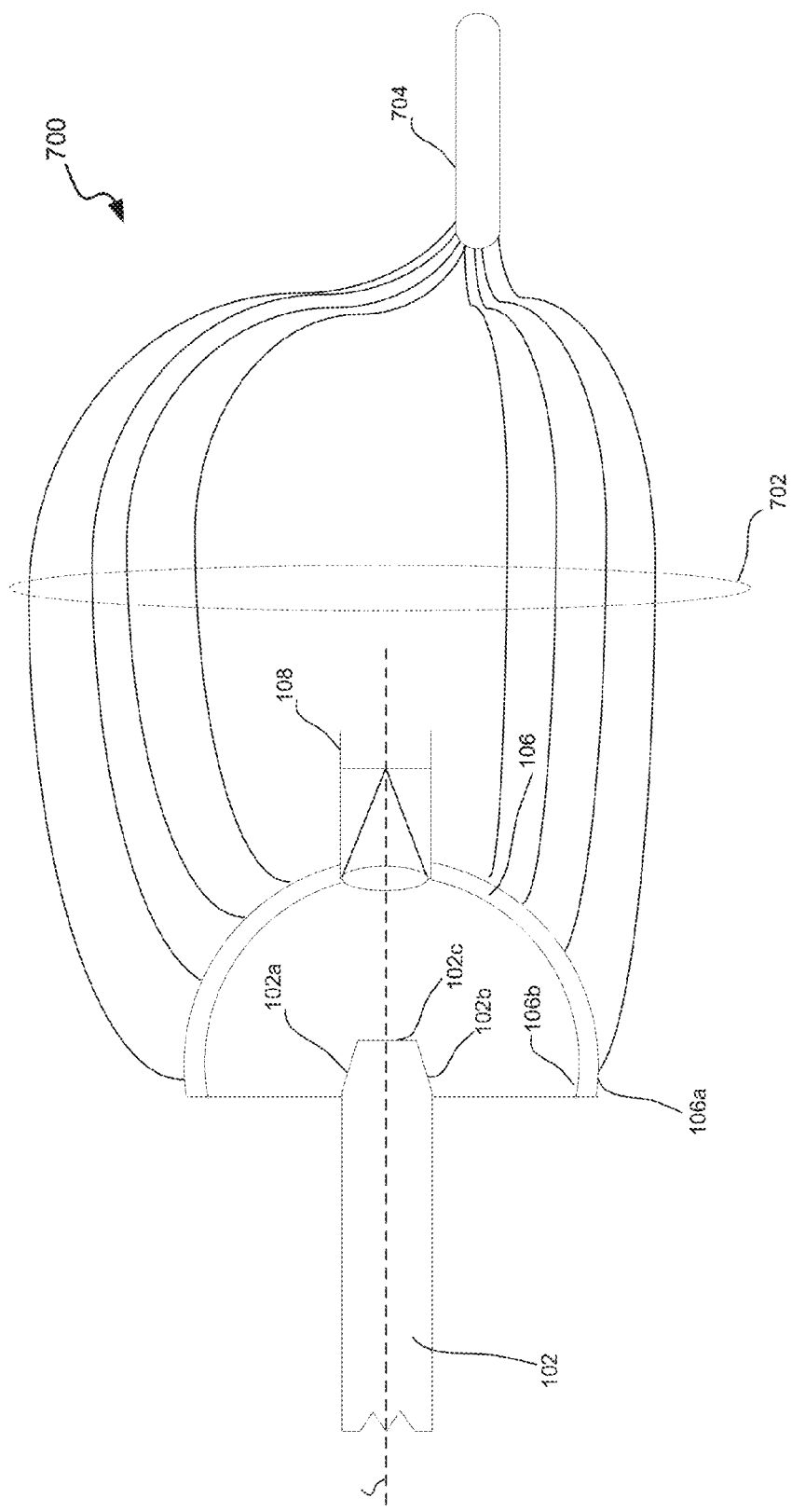
FIG. 7 is a diagrammatic representation of an edge detection system that utilizes optical fiber bundles in accordance with an alternative implementation of the present invention.

In an alternative embodiment, the edge detection system can direct illumination from one or more remote light sources to the diffuser through a plurality of optical fibers. FIG. 7 is a diagrammatic representation of an edge detection system 700 that utilizes optical fiber bundles in accordance with an alternative implementation of the present invention. As shown, a light source 704 (or multiple light sources) generates illumination for a plurality of fibers 702. One end of each fiber 702 is adjacent to the light source 704, while the opposite end of each fiber 702 is positioned proximate to a particular position of the diffuser 106. That is, the fibers 702 provide individual light sources at different positions on the external surface 106a of the diffuser 106. Each fiber outputs light into the diffuser at its corresponding location, and such light is scattered and diffused by the diffuser 106 as described above.

Figure 8:
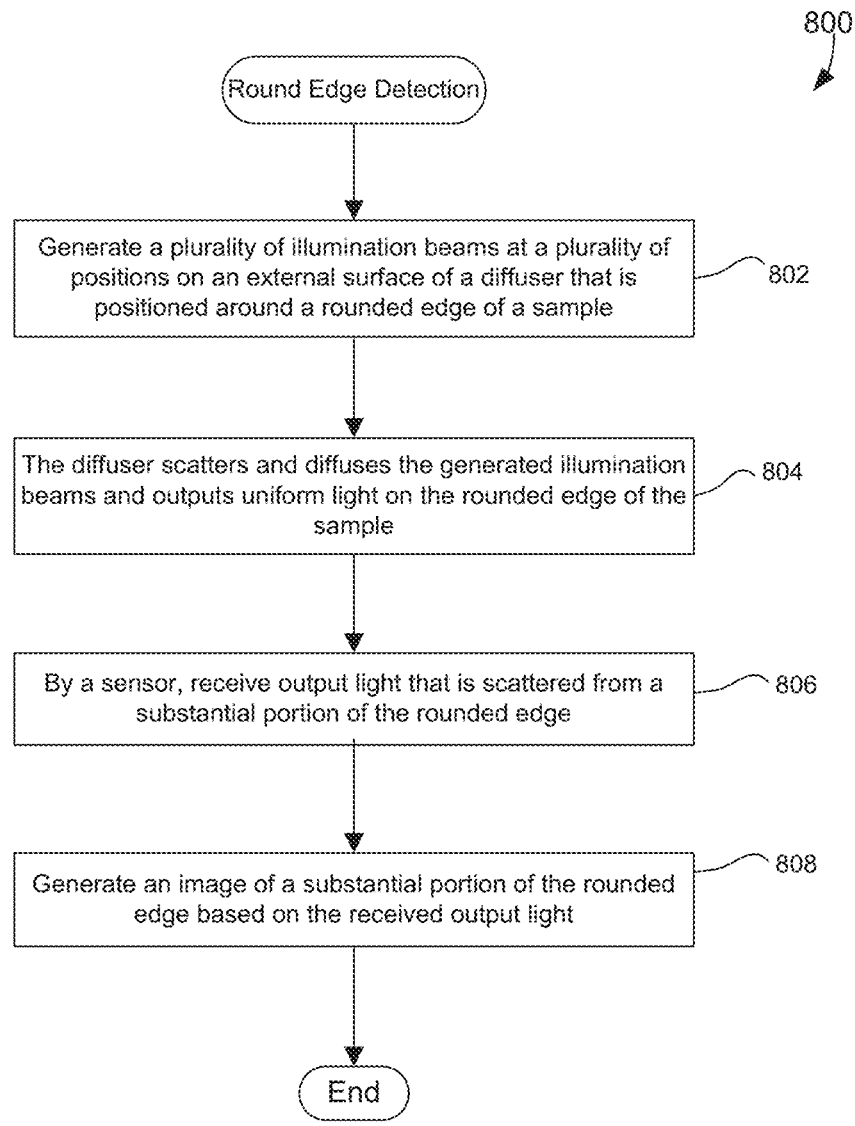
FIG. 8 is a flow chart illustrating a round edge detection process in accordance with one embodiment of the present invention.

FIG. 8 is a flow chart illustrating a round edge detection process 800 in accordance with one embodiment of the present invention. Initially, a plurality of illumination beams (or light sources) may be generated at a plurality of positions on an external surface of a diffuser that is positioned around a rounded edge of a sample in operation 802. The diffuser scatters and diffuses the generated illumination beams and outputs uniform light onto the rounded edge of the sample (for example, at multiple incident angles as described above) in operation 804.

Output light that is scattered from a substantial portion of the rounded edge is then received by a sensor (or multiple sensors) in operation 806. An image of the substantial portion of the rounded edge may then be generated based on the received output light in operation 808.

Figure 9:
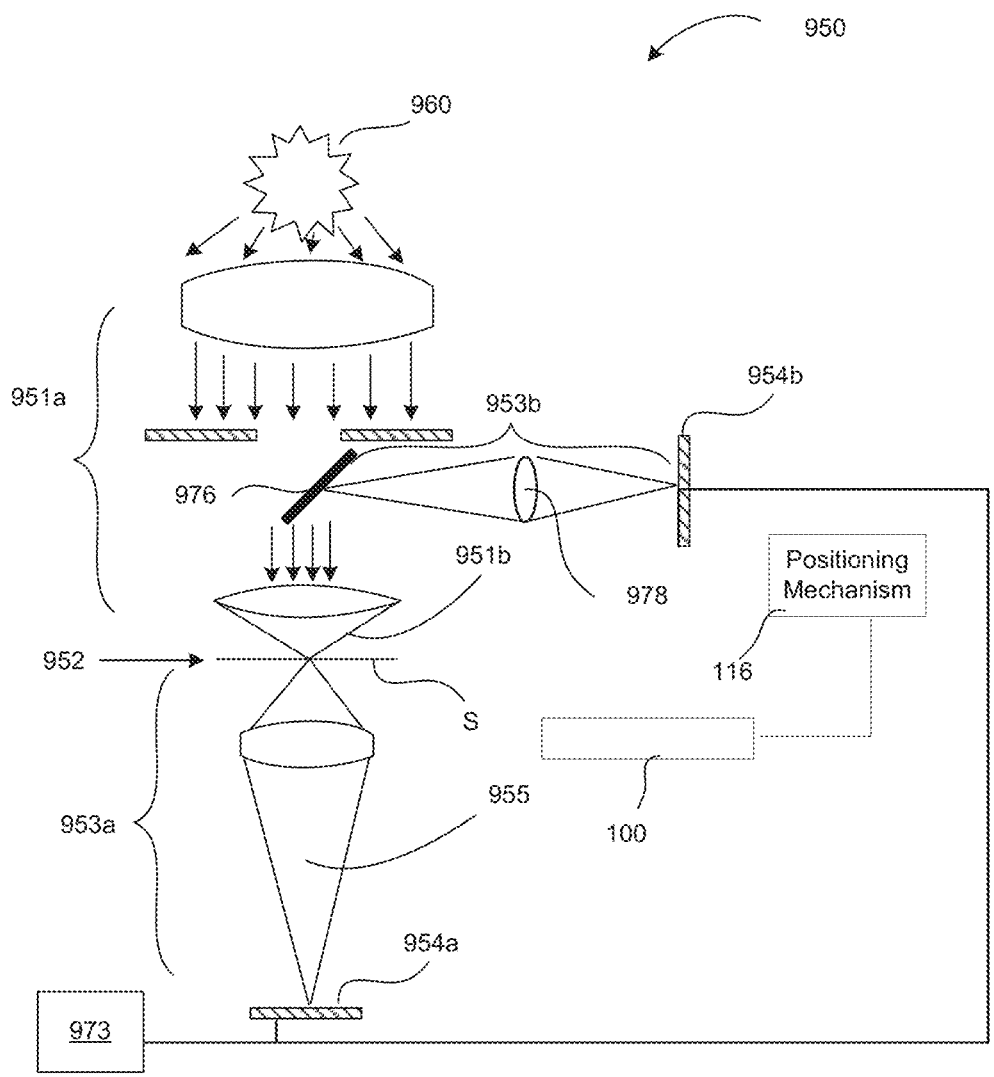
FIG. 9 provides a schematic representation of an inspection apparatus in accordance with certain embodiments.

The edge detection systems and methods described herein may be integrated into any suitable optical imaging system. The edge detection system may be integrated into various specially configured inspection or review systems, such as the inspection system 950 schematically illustrated in FIG. 9. This inspection system 950 may include components for inspecting a top surface of sample S, as well as components for imaging the edge of sample S.

For the top surface, the illustrated system 950 includes an illumination source 960 producing a light beam that is directed through illumination optics 951a onto a sample S, such as a reticle or wafer, in plane 952. Examples of light sources include a coherent laser light source (e.g., deep UV or gas laser generator), a filtered lamp, LED light source, etc. The sample S to be inspected is placed on a stage at plane 952 and exposed to the source.

The patterned image from sample S (e.g., for a reticle) may be directed through a collection of optical elements 953a, which project the patterned image onto a sensor 954a. In a reflecting system, optical elements (e.g., beam splitter 976 and detection lens 978) direct and capture the reflected light onto sensor 954b. Although two sensors are shown, a single sensor can be used to detect reflected and transmitted light during different scans of the same reticle area. Suitable sensors include charged coupled devices (CCD), CCD arrays, time delay integration (TDI) sensors, TDI sensor arrays, photomultiplier tubes (PMT), and other sensors.

The illumination optics column may be moved respect to the stage and/or the stage moved relative to a detector or camera by any suitable mechanism so as to scan patches of the sample S. For example, a motor mechanism may be utilized to move the stage. The motor mechanism may be formed from a screw drive and stepper motor, linear drive with feedback position, or band actuator and stepper motor, by way of examples.

For the edge, the inspection system 950 may also include edge detection system (e.g., 100) as described above. Any of the edge detection systems may be used within inspection system 950 to image an edge of sample S. The inspection system 950 may also include a positioning mechanism 116 for moving the edge detection system to a position to image the edge as described above.

The signals captured by each sensor (e.g., 954a and 554b of the inspections system and the sensor of the edge detection system 100) can be processed by a computer system 973 or, more generally, by a signal processing device, which may include an analog-to-digital converter configured to convert analog signals from the sensors into digital signals for processing. The computer system 973 may be configured to analyze intensity, phase, images and/or other characteristics of a sensed light beam. The computer system 973 may be configured (e.g., with programming instructions) to provide a user interface (e.g., on a computer screen) for displaying images and other inspection characteristics. The computer system 973 may also include one or more input devices (e.g., a keyboard, mouse, joystick) for providing user input, such as changing detection threshold, focus, etc. In certain embodiments, the computer system 973 is configured to carry out inspection techniques detailed below. The computer system 973 typically has one or more processors coupled to input/output ports, and one or more memories via appropriate buses or other communication mechanisms.

Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

In certain embodiments, a system for inspecting a sample includes at least one memory and at least one processor that are configured to perform the above described techniques and/or to operate the inspection tool.

It should be noted that the above diagrams and description are not to be construed as a limitation on the specific components of the system and that the system may be embodied in many other forms. For example, it is contemplated that the inspection or measurement tool may be any of a number of suitable and known imaging or metrology tools arranged for resolving the critical aspects of features of a reticle or wafer. By way of example, an inspection or measurement tool may be adapted for bright field imaging microscopy, darkfield imaging microscopy, full sky imaging microscopy, phase contrast microscopy, polarization contrast microscopy, and coherence probe microscopy. It is also contemplated that single and multiple image methods may be used in order to capture images of the target. These methods include, for example, single grab, double grab, single grab coherence probe microscopy (CPM) and double grab CPM methods. Non-imaging optical methods, such as scatterometry, may be contemplated.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. Accordingly, the present embodiments are to be considered as illustrative and not restrictive, and the invention is not to be limited to the details given herein.

What is claimed is:

1. A system for imaging a rounded edge of a sample, comprising:

a curved diffuser having an internal surface for positioning towards the rounded edge of the sample and an external surface opposite the internal surface;

a plurality of light sources for generating a plurality of illumination beams adjacent to a plurality of positions on the external surface of the diffuser so that the diffuser outputs uniform light over the rounded edge of the sample at a plurality of incident angles, wherein the light sources are abutting the diffuser; and a sensor for receiving light scattered from the rounded edge of the sample in response to the incident light and generating a detected signal for generating an image, wherein the sensor is positioned within or adjacent to a hole of the diffuser, wherein the light sources, diffuser, and sensor are integrated into a compact format.

2. The system of claim 1, wherein the sensor has a diameter that is equal to or less than 3 mm.

3. The system of claim 1, wherein the diffuser is dome shaped.

4. The system of claim 1, wherein the sample is a wafer and the edge is a beveled edge of such wafer, and wherein the diffuser is shaped and sized to output uniform light over all the surfaces of the beveled edge.

5. The system of claim 4, wherein the uniform light also covers a border area of the top surface of the wafer.

6. The system of claim 5, wherein the sensor is positioned in the diffuser with respect to the light sources so as to receive light scattered from a particular set of one or more surfaces of the beveled edge.

7. The system of claim 1, wherein the sensor is mounted or bonded within the hole of the diffuser.

8. The system of claim 7, wherein the sensor is recessed in the hole and with respect to the internal surface of the diffuser.

9. The system of claim 1, further comprising a positioning mechanism to adjustably move the diffuser, light sources, and sensor to different positions so as to image different sets of one or more surfaces of the rounded edge.

10. The system of claim 1, wherein the light sources are positioned a distance between about 3 mm and 1 inch from the external surface of the diffuser.

11. The system of claim 1, further comprising a support structure to which the light sources are affixed.

12. The system of claim 1, wherein the light sources are LED's (light emitting diodes) that are affixed to the external surface of the diffuser.

13. The system of claim 1, wherein the diffuser includes slots through which the sample may be inserted, the system further comprising a positioning mechanism for rotating the diffuser, light sources, and sensor in a plane that is parallel with the slots so that the sample moves through the slots of the diffuser and the sensor receives light from different incident angles.

14. The system of claim 1, further comprising a plurality of sensors inserted in a plurality of holes of the diffuser to receive light at different incident angles.

15. The system of claim 1, wherein the light sources are in the form of a plurality of optical fibers for directing light from one or more light generators.

16. The system of claim 1, wherein the light sources are composed of electronic components for generating the illumination beams directly onto the diffuser without transporting such illumination beams to the diffuser via any optical elements.

17. An inspection system for inspecting a sample, comprising:

the system for imaging a rounded edge a sample as recited in claim 1;

inspection optics for directing one or more second illumination beams towards a top surface of the sample;

an inspection detector for receiving a detected signal or image in response to an output beam being scattered or reflected from or transmitted through the sample in response to the output beam being reflected or scattered from the sample; and a processor and memory that are configured to analyze or review the detected signal or image from the inspection detector to thereby detect defects on the sample and configured to analyze the detected signal or image from the system for imaging the rounded edge of the sample to thereby detect defects on a rounded edge of a sample.

18. The system of claim 17, wherein the light sources are composed of electronic components for generating the illumination beams directly onto the diffuser without transporting such illumination beams to the diffuser via any optical elements.

19. The system of claim 17, wherein the light sources are LED's (light emitting diodes) that are affixed to the external surface of the diffuser.

20. The system of claim 17, wherein the light sources are in the form of a plurality of optical fibers for directing light from one or more light generators.

\* \* \* \* \*